US007034934B2

(12) United States Patent
Manning

(10) Patent No.: US 7,034,934 B2
(45) Date of Patent: Apr. 25, 2006

(54) ANTI-CARCINOGENIC LIGHTS AND LIGHTING

(75) Inventor: Roy O. Manning, Vero Beach, FL (US)

(73) Assignee: Neway Systems & Products, Inc., Vero Beach, FL (US)

( * ) Notice: Subject to any disclaimer, the term of this patent is extended or adjusted under 35 U.S.C. 154(b) by 0 days.

(21) Appl. No.: 10/749,092

(22) Filed: Dec. 30, 2003

(65) Prior Publication Data

US 2005/0146278 A1 Jul. 7, 2005

(51) Int. Cl.
*A61K 49/00* (2006.01)

(52) U.S. Cl. ........................ 356/326; 424/9.1; 315/149

(58) Field of Classification Search ................ 315/224, 315/291, 149–159; 356/319, 320, 326, 328, 356/330; 362/30, 572–574, 230, 231; 424/9.1, 424/133.1, 130.1, 138.1, 141.1; 250/472.1, 250/474.1

See application file for complete search history.

(56) References Cited

U.S. PATENT DOCUMENTS 6,649,143 B1 * 11/2003 Contag et al. ............... 424/9.1
6,781,691 B1 * 8/2004 MacKinnon et al. ........ 356/326

OTHER PUBLICATIONS

Olin, "Color Cognition," *The New York Times*, Nov. 30, 2003, 2 pages.
Ivry, "Seasonal Depression Can Accompany Summer Sun," *The New York Times*, Aug. 13, 2002, 4 pages.
"Melatonin," *Life Extension*, Abstracts section, Mar. 2002, pp. 79-81.
"Melatonin and Cancer," *Life Extension*, In the News section, Jun. 2001, pp. 17-18.
Nagourney, "Of Light, Tissue an Better Moods," *The New York Times*, Apr. 24, 2001, 1 page.
Reuters, "Matching Light to Internal Clock Fights Depression," *The New York Times*, Jan. 23, 2001, 2 pages.

(Continued)

*Primary Examiner*—Wilson Lee
(74) *Attorney, Agent, or Firm*—Brian S. Steinberger; Law Offices of Brian S. Steinberger, P.A.

(57) ABSTRACT

Devices and methods for using visible light of wavelengths between 760 to 610 nanometers, here termed Anti-Carcinogenic™ or CancerSafe™ or CancerGuard™ light. When irradiated upon animals during their customary sleeping hours, or when they are sleepy, or have been sleeping, Anti-Carcinogenic™ night light does not disrupt the hormonal secretions of the pineal gland. Conventional light, associated with pollution of the sky and urban areas, disrupts hormonal secretions, and much evidence points to hormonal secretion disruptions as a cause of cancer. The novel Night Lights can illuminate areas adjacent bedrooms, dormitories, and in vehicles, buses, aircraft, where passengers customarily sleep, and in refrigerators, and on illuminated clocks and watches. These Night Lights can have back-up power supply and employ motion sensors and photoelectric switches to switch on Anti-Carcinogenic™ (non-carcinogenic) illumination when needed for safe movement in otherwise darkened areas, and can detect power failures, noises indicative of violence, such as panics, school shootings, cries for help in medical emergencies, or assaults, and also detect dangerous, toxic, or explosive substances, including particulates, bacteria, viruses, thereupon they communicate alarms by sound, optical cable, laser, or radio frequency. Also covered are devices converting conventional carcinogenic night lights to Anti-Carcinogenic™ ones, and translucent window drapes and light traps to convert other light sources to Anti-Carcinogenic™ light.

19 Claims, 6 Drawing Sheets

OTHER PUBLICATIONS

Goode, "Melatonin Used to Restore Sleep Patterns in Blind People," *The New York Times*, Jun. 22, 1999, 3 pages.

McAuliffe, "Researchers Shine a Night Light on a Possible Link to Cancer," *The New York Times*, Jun. 13, 1999, 3 pages.

Brainard, "The Biological and Therapeutic Effects of Light," Chapter 9, *Color for Science, Art and Technology*, 1998 Elsevier Science B.V., pp. 247-270.

Brainard, et al., "The Healing Light: Interface of Physics and Biology," *Seasonal Affective Disorder and Beyond*, American Psychiatric Press, Inc., 1998, pp. 1-44.

Brainard, et al., "Ultraviolet Regulation of Neuroendocrine and Circadian Pysiology in Rodents," *Vision Res.* vol. 34, No. 11, pp. 1521-1533, Oct. 6, 1993.

Brainard, et al., "Effect of Light Irradiance and Wavelength on the Syrian Hamster Reproductive System," *Endocrinology*, vol. 119, No. 2, Oct. 22, 1985, pp. 648-654.

Brainard, et al., "The Influence of Different Light Spectra on the Suppression of Pineal Melatonin Content in the Syrian Hamster," *Brain Research*, 294 (1984) pp. 333-339, Elsevier.

* cited by examiner

ANTI-CARCINOGENIC LIGHTS AND LIGHTING

This invention relates to lights and lighting, in particular to devices and methods for applying various wavelengths of light as a non-carcinogenic visible light source

BACKGROUND AND PRIOR ART

Numerous experiments document that hormonal changes are carcinogenic and the Federal government has recently ceased supporting hormonal replacement therapy (HRT) for this reason. It is therefore not surprising that disruptions of nocturnal hormonal secretions of the pineal gland are also carcinogenic. Cf. Schernhammer, E. S., et alia, "Rotating night shifts and risk of breast cancer in women participating in the nurses' health study." Journal of the National Cancer Institute 2001 Oct. 17; 93 (20): 1563–1568; Davis, S., et alia, "Night shift work, light at night, and risk of breast cancer." Journal of National Cancer Institute 2001 Oct. 17; 93 (20) 1557–1562. Also see papers published in the Journal of Pineal Research 1993 August; 15 (1): 1–12; Melanoma Research 1991 November-December; 1 (4): 237–43; Oncology 1992; 49 (5): 336–9; and the European Journal of Cancer 1999 November; 35(12):1688–92. Abstracts of the above papers were published in Life Extension Magazine, March 2002, pp. 79–81. Also see the remarks of D. Blask, Ph.D., G. C. Brainard, Ph.D., and R. Stevens, Ph.D., quoted by Kathleen McAuliffe in, "Researchers shine a night light on a possible link to cancer." New York Times on the Web, Women's Health section, 1999 Jun. 13. This article and correspondence between the inventor and researchers G. C. Brainard, Ph.D, R. J. Reiter, Ph.D., and C. A. Czeisler, Ph.D. are enclosed.

The pineal gland in the brain secretes the hormone melatonin. Melatonin has a powerful effect on the circadian rhythms and is involved in the illness called Seasonal Affect Disorder, or SAD. The secretions are synchronized so that high levels of melatonin are released during the night and low levels during the day. Disruption of the nocturnal secretions of this hormone has many ill effects, principally through its effects on other glands. Cf. W. Pierpaoli, W. Regelson, The Melatonin Miracle. NY: Simon & Schuster, Inc., 1995; Abdel-Wanis, M. E., et alia, "Aetiology of spinal deformities in neurofibromatosis 1: new hypotheses." Medical Hypotheses 2001 March; 56 (3): 400–404. Grin, W., et alia, "A significant correlation between melatonin deficiency and endometrial cancer." Gynecological Obstetrical Investigation 1998; 45 (1): 62–65. Grad, B. R., et alia, "The role of melatonin and serotonin in aging: update." Psychoneuroendocrinology 1993; 18 (4): 283–295. Sandyk, R., et alia, "Is the pineal gland involved in the pathogenesis of endometrial carcinoma." International Journal of Neuroscience 1992 January; 62 (1–2): 89–96.

Research during the past ten to fifteen years confirmed that light entering the eyes is a powerful means of controlling the circadian system in humans. Aside from neurological signals sent from the retina to the visual centers of the brain, other such signals are sent to the hypothalamus and it is these that greatly effect the hormonal secretions of the pineal gland. Cf. G. C. Brainard, et alia, "Dose-response relationship between light irradiance and the suppression of plasma melatonin in human volunteers." Brain Research, 454 (1988), pp. 212–218.

The sleep patterns of even totally blind people are affected by the absence of retinal exposure to light. This was established in the 1970's by James Stevenson, then a blind graduate student at Stanford University. It was later confirmed by Laughton Miles, Ph.D., who published a paper in 1977 on the subject of the effect of light on the blind. In 1987 Dr. James Stevenson began taking doses of the hormone secreted by the pineal gland, melatonin, with great success in that it enabled him to establish regular sleep patterns, which is a difficulty in total blindness. Cf. E. Goode, "Melatonin used to restore sleep patterns in blind people." New York Times on the Web, 27 Jun. 1999.

Regardless of the entry path of light, whether through exposed body tissue or directly, through the retina of the eye, light disrupts the secretions of the pineal gland. Cf. E. Nagoumey, "Of Light, Tissue, and Better Moods," New York Times on the Web, 24 Apr. 2001, which cites the work of D. Oren, Ph.D. of Yale University, published recently in Biological Psychiatry.

If the pineal gland is secreting melatonin, exposure to ordinary light will disrupt its secretions. Cancers become common with disruptions of pineal secretion during the hours customarily devoted to sleep. In humans, cancers of the breast, prostate, and colon are most likely since these are already the most common. It is irrelevant that light striking the retina may only be faint and the exposure last only a second. The light may be from outside security lighting, a distant street lamp penetrating drapes or shutters, an ordinary household night light, or even from the moon.

SUMMARY OF THE INVENTION

A primary objective of the present invention is to provide devices and methods that provide Anti-Carcinogenic™ light in areas darkened for sleeping. Such Anti-Carcinogenic™, CancerSafe™, or CancerGuard™ light should also be displayed on watches with lighted dials worn while sleeping.

A secondary objective of the present invention is to provide lighting,systems, methods, and devices to convert lights and lighting of conventional wavelengths to that of Anti-Carcinogenic™ light in areas otherwise darkened for sleeping. Anti-Carcinogenic™ lighting would automatically be turned off by photo-electric cell controlled switch(es) when conventional illumination is provided. In areas darkened for sleeping, motion sensors would automatically turn on Anti-Carcinogenic™ lights or lighting when the presence of humans or animals of a predetermined size are detected. Such Anti-Carcinogenic™ lights and lighting would be protected against surges in electrical currency, so they would not be disabled in the event of electrical storms or power failures.

A third objective of the present invention is to provide devices and methods to equip appliances like refrigerators, microwaves, cupboards and other appliances and devices that automatically display carcinogenic light when opened so they will display only Anti-Carcinogenic™ light when opened up or operated in otherwise darkened or near-darkened rooms. When located in darkened or near-darkened areas, and in the presence of humans or animals of a predetermined size, such appliances and devices would display Anti-Carcinogenic™ night light(s) on their exteriors, thereby serving as Anti-Carcinogenic night™ lights.

A fourth objective of the present invention is to provide devices and methods to provide Anti-Carcinogenic™ interior lighting in place of ordinary lighting, thereby to minimize jet lag in buses, ferries, aircraft, or spacecraft over long passages by allowing passengers and crew to sleep without disruption of the secretions of their pineal glands.

A fifth objective of the present invention is to provide devices and methods to convert ordinary carcinogenic lights and lighting in sleeping areas to Anti-Carcinogenic™ lights and lighting by means of translucent plastic, glass, fabric, or ceramic CancerGuard shield(s)™. These would cover or otherwise enclose sources of daylight and ordinary lighting and thereby convert them into sources of Anti-Carcinogenic™ light.

A sixth objective of the present invention is to provide devices and methods that incorporate devices that will indicate the occurrence of power failures and actuate back-up batteries.

A seventh objective of the present invention is to provide devices and methods that detect and warn of dangerous levels of smoke, heat, carbon monoxide, carbon dioxide, radon gas, radioactive effects, oxygen, explosive particulars or vapors such as propane or methane, or noxious or poisonous gases.

An eighth objective of the present invention is to provide devices and methods for dipping, staining, or otherwise coating sources of ordinary light in sleeping areas so they emit Anti-Carcinogenic™ light. Substances deposited by dipping, staining, or otherwise coating ordinary sources of light will resist becoming carbonized and thereby losing effectiveness.

As previously described, hormonal changes can cause cancer. Thus Hormonal Replacement Therapy (HRT) is now considered dangerous by the Federal government. Disruptions of pineal gland secretions of melatonin during customary, usually nocturnal, sleeping hours cause cancers. Visual light other than that occurring between the wavelengths of 760 to 610 nanometers, disrupts these secretions. Light between these wavelengths is referred to as Anti-Carcinogenic™, CancerSafe™, or CancerGuard™ light. Such light appears red or reddish too many people but this is a strictly subjective description and insufficiently precise for scientific purposes or industrial applications.

The present invention teaches a novel use for light of wavelengths between approximately 760 to approximately 610 nanometers. It teaches that light between these wavelengths will not disrupt secretions of the pineal gland, and thus will not cause cancers, but still may be used for all the usual purposes of visual light. Jet lag is a malady which involves disruption of the secretions of the pineal gland through exposure to unaccustomed hours of darkness and light. In vehicles where passengers customarily sleep, such as buses, ferries, railroads, aircraft or spacecraft, jet lag may be greatly reduced by the use of Anti-Carcinogenic™, CancerSafe™, or CancerGuard™ lighting. The use of Anti-Carcinogenic™, CancerSafe™, or CancerGuard™ lighting will maximize the period during which the pineal gland secretes melatonin. Cf. G. C. Brainard, "The Healing Light: Interface of Physics and Biology," pp. 1–44 in, Seasonal Affective Disorder and Beyond, 1998, R. W. Lam, ed., American Psychiatric Press; also see, Healthnotes Online; Melatonin, 6 Nov. 2001.

The extent to which jet lag can be reduced will depend on the time spent in travel and the latitudes and longitudes of departure and arrival. In either case, use of Anti-Carcinogenic™ lighting would allow passengers and crewmen to better meet the customary demands of their bodies for sleep, or be able to accumulate extra rest if used throughout the passage. Passengers would arrive more rested and better able to deal with demands placed on them in the new time zone.

Further objects and advantages of this invention will be apparent from the following detailed description of the presently preferred embodiments which are illustrated schematically in the accompanying drawings.

DESCRIPTION OF THE PREFERRED EMBODIMENTS

Figure 1:
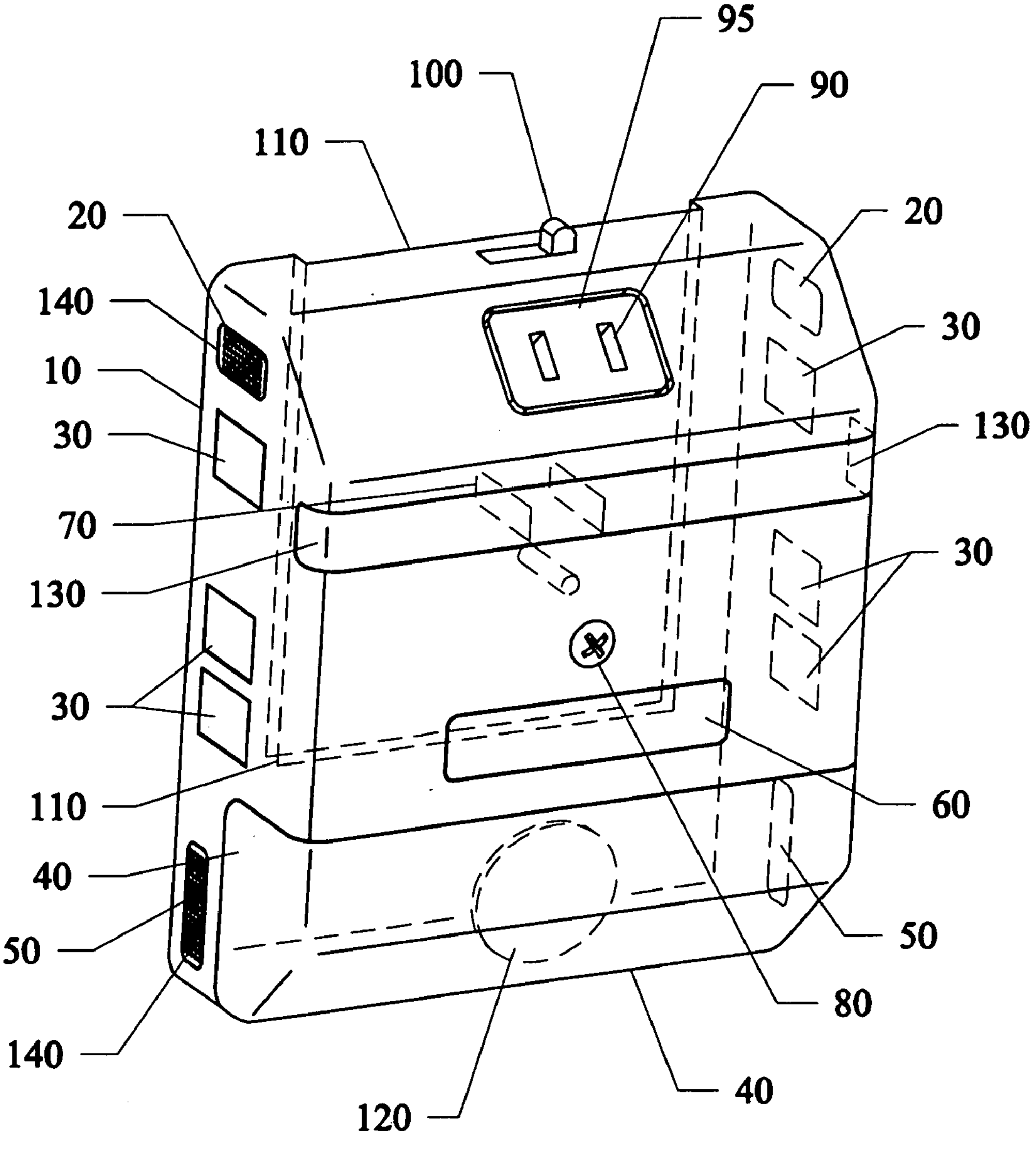
FIG. 1 is a perspective view of an Anti-Carcinogenic™ Night Light invention.

Before explaining the disclosed embodiments of the present invention in detail it is to be understood that the invention is not limited in its applications to the details of the particular arrangements shown since the invention is capable of other embodiments. Also, the terminology used herein is for the purpose of description and not of limitation.

REFERENCE NUMERALS AND THEIR CORRESPONDING LABELS

10 Outer Case
15 AC Power Supply
20 Atmosphere Sample Exhaust
30 Monitor Detector Insertion Port(s) 30
40 Anti-Carcinogenic™ Light Window
50 Atmosphere Sample Intake
60 Photo-electric Cell
70 Receptacle Prongs (to AC Power Source 15)
80 Child-Safe Screw
85 Receptacle Box Cover Plate
90 Auxiliary Receptacle
95 Auxiliary Receptacle Cover Plate
100 Power Switch Manual Over-ride
110 Outer Case Back Recess (receives Auxiliary Receptacle Cover Plate 95)
120 Anti-Carcinogenic™ Light Source
130 Motion Sensor Window
140 Flame Proof Screen (fine metallic gauze preventing ignition of flammable vapors, as used in the Flame Safety Lamp)
150 Electro-Magnetic Switch
155 Magnetically Actuated Switch
157 Dielectric Short Circuit Barrier
160 Photo-Electric Cell Switch
170 Motion Sensor Switch
180 Radio Transmitting Alarm
190 Alarm Bell
200 DC Battery
210 Fan
220 Monitor Detectors (of dangerous gases, vapors, smoke, radiological, or biologically active substances)
230 A C Surge Protector
250 Refrigeration Mechanism
260 Refrigerator Conventional Interior Light
270 Refrigerator Internal Anti-Carcinogenic™ Light Source 280 Refrigerator External Anti-Carcinogenic™ Light Source
290 Refrigerator Door Switch
300 Solar Power Source
320 Filter Hood
330 Base Plate
340 Conventional Carcinogenic™ Night Light
350 Plate Securing Hole
355 Base Plate Prong Slot(s)
360 Raised Plane
370 Prong Access Port(s)

The inventor has deduced that light between the wavelengths of approximately 760 to approximately 610 nanometers (nm)will not suppress the nocturnal secretions of the pineal gland. The subject inventor's own research and subsequent correspondence with leading researchers (noted above) confirms this. The inventor therefore has concluded that during the hours devoted to sleep, light limited to the above range of wavelengths will not be carcinogenic: since it does not suppress the secretions of the pineal gland of humans and mammals.

Relying on this observation, the present invention teaches a new use for visual light between these wavelengths, to wit, it may be used to provide Anti-Carcinogenic™, Cancer-Safe™, or CancerGuard™ night lights and lighting in sleeping areas. Anti-Carcinogenic™, or CancerSafe™, or CancerGuard™ light is defined here as visual light between the wavelengths of approximately 760 and approximately 610 nanometers. Such light usually appears red or reddish to persons with normal color vision.

However, since impressions and descriptions of colors are subjective and thus vary considerably, definition in terms of wavelength is preferable. Such definition is unambiguous, definitive, and facilitates experimental replication. Therefore, Anti-Carcinogenic™, CancerSafe™, or CancerGuard™ light is defined in terms of its occurring between the wavelengths of approximately 760 and approximately 610 nanometers. As noted such light usually appears red or reddish to persons with normal color vision. However, since impressions and descriptions of colors are subject to cultural, linguistic, and subjective interpretation. Olin, Dirk, "Color Cognition", New York Times, 30 Nov. 2003. Thus, definition by wavelength is preferable since it facilitates experimental replication. Therefore, Anti-Carcinogenic, CancerSafe, or CancerGuard light is defined in terms of its occurring between the wavelengths of approximately 760 and 610 approximately nanometers.

Anti-Carcinogenic Night Light

FIG. 1 is a perspective view of an Anti-Carcinogenic™ Night Light invention. The Outer Case 10 of the preferred embodiment Anti-Carcinogenic™ Night Light can have a Motion Sensor Window 130 and a Photo-electric Cell 60. The lower one-third of the Outer Case 10 has a Anti-Carcinogenic™ Light Window 40 behind Light Source 120 such as a bulb, Light-Emitting Diode or other Anti-Carcinogenic™ light emitting source.

Figure 2:
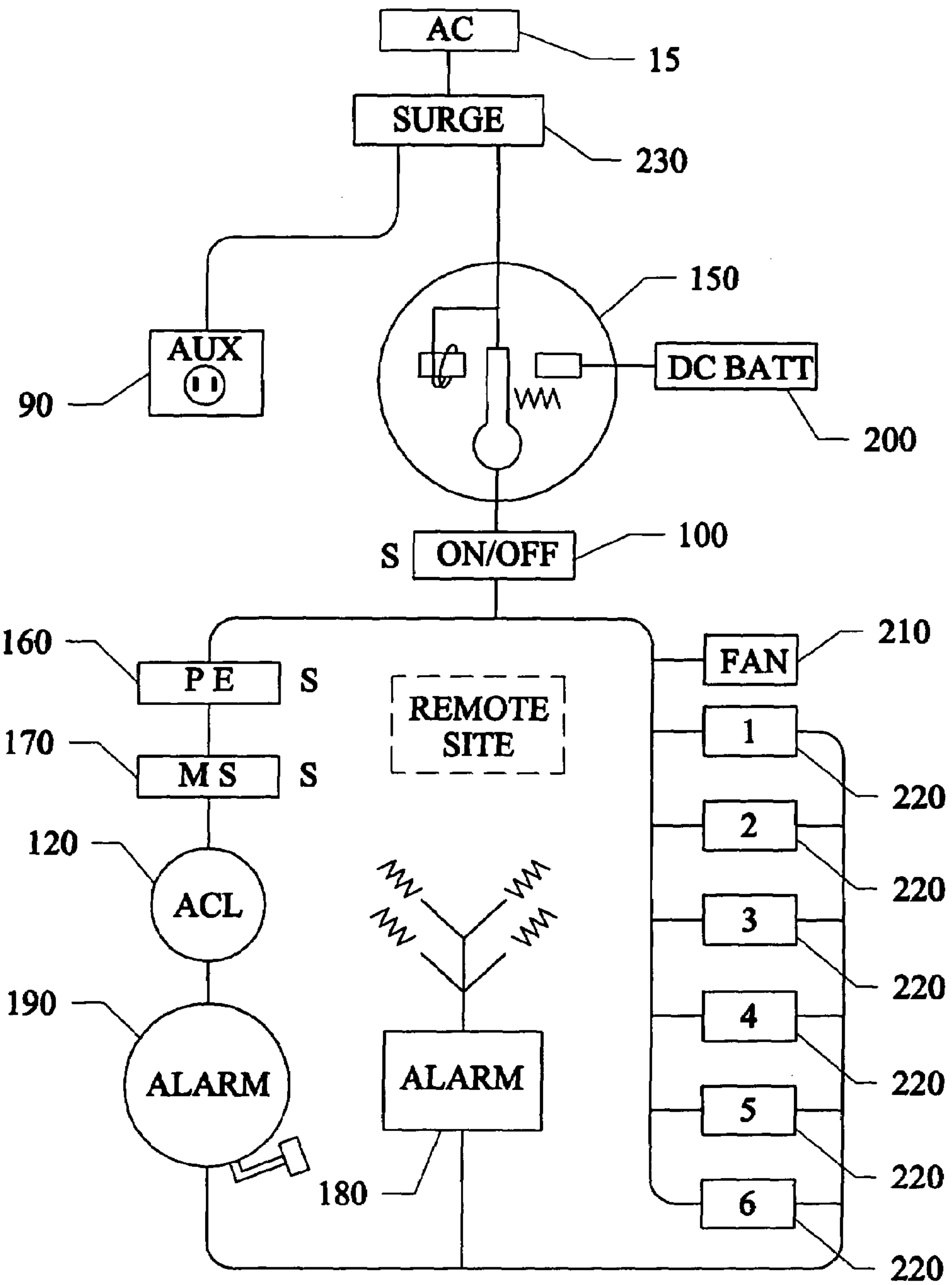
FIG. 2 is an electric flow diagram for the Anti-Carcinogenic™ Night Light of FIG. 1.

A Power Switch Manual Over-ride 100 can be used to shut off all operation of the Anti-Carcinogenic™ Night Light. Receptacle Prongs 70 can protrude from the rear of the Outer Case 10 for insertion into a wall receptacle AC Power Supply 15, which is shown in FIG. 2. The case can be molded from plastic, and the like, and have dimensions of approximately 3 to approximately 12 inches in height, approximately 3 to approximately 12 inches wide, by approximately 2 to approximately 4 inches in thickness. The case can also be made from other materials, such as but not limited to glass, ceramic, metal such as bronze, and the like, and combinations, thereof, with a translucent face for allowing visible light to pass therethrough.

In a child-safe arrangement, the device can be semi-permanently affixed to its AC Power Supply 15 receptacle box such as a 120 volt power supply through a wall outlet using a special Child-Safe Screw 80 which passes through the receptacle box cover and screws into the center of the receptacle box. This prevents the Anti-Carcinogenic™ Night Light from being easily pulled out of its receptacle box to expose the AC Power Supply 15 receptacle.

FIG. 2 is an electric flow diagram for the Anti-Carcinogenic™ Night Light of FIG. 1. Referring to FIGS. 1-2, an Auxiliary Receptacle 90 is supplied in the Outer Case 10 so that other appliances can be plugged into the Anti-Carcinogenic™ Night Light. An Auxiliary Receptacle Cover Plate 95 is supplied as a child-safety device. In operation, air is drawn in through the Atmosphere Sample Intake 50 where it would normally be sufficiently heated by the Anti-Carcinogenic™ Light Source 120 so that it will rise and pass over the array of six (6) Monitor Detectors 220, shown in FIG. 2, for detecting dangerous gases, vapors, smoke, radiological, or biological active substances, and the like, and combinations thereof. One or more of the Monitor Detectors 220 can be converted to serve as microphones to receive abnormal noises associated with violence, such as shooting, cries for medical attention, or protesting the commission of an assault. To assure upward circulation of air in warmer atmospheres or in a strong wind, a Fan 210 can be supplied, as shown in FIG. 2.

The Monitor Detector Insertion Port(s) 30 can be seen along each side of the Outer Case 10 FIG. 1. The sampled atmosphere leaves the Outer Case 10 at the Atmosphere Sample Exhaust 20. Both the Atmosphere Sample Intake 50 and the Atmosphere Sample Exhaust 20 are fitted with Flame Proof Screen 140, i.e., fine metallic gauze mesh to dissipate heat, thereby to prevent sparks from static electricity or the Electro-Magnetic Switch 150 igniting an explosive mixture should such be drawn into the Outer Case 10.

Referring to FIG. 2, the Anti-Carcinogenic™ Night Light normally requires an AC Power Supply 15. This can be fed directly to an AC Surge Protector 230 and then led to both the Auxiliary Receptacle 90 and to an Electro-Magnetic Switch 150 which is designed to supply Direct Current from a back-up DC Battery 200 if the AC Power Supply 15 fails. In operation, a portion of the current from the AC Power Supply 15 is converted to DC in order to energize an electromagnet within the Electro-Magnetic Switch 150. Thus, when AC Power Supply 15 is available, the electromagnet within the Electro-Magnetic Switch 150 pulls the contact over to divert AC Power Supply 15 to the units of the Anti-Carcinogenic™ Night Light. If AC Power Supply 15 is not available, and the electromagnet within the Electro-Magnet Switch 150 is not energized, then an internal metal spring within the Electro-Magnetic Switch 150 pulls the switch over to connect with power supplied by the DC Battery 200, such as a 12 volt battery power source.

Regardless of how power is supplied, AC or DC, the power is led to the Power Switch Manual Over-ride 100 and thence to the locations where it is employed, namely, to operate a Fan 210 to assure circulation of ambientar so samples can be tested by passing them across six (6)Monitor Detectors 220 for detecting selected threshold evidence of dangerous gases, vapors, smoke, radiological, or biologically active substances, such as but not limited to Anthrax, and the like, above selected threshold levels. Power is simultaneously supplied to the Photo-electric Cell Switch 160, the Motion Sensor Switch 170 and to the Anti-Carcinogenic™ Light Source 120 itself. In the event that any of the six (6) Monitor Detectors 220, sense any evidence of such substances such as but not limited to dangerous gases, vapors, smoke, radiological, biological active substances in the atmosphere, or noises indicative of violence, a circuit across the relevant Monitor Detector 220 is closed and power can then be supplied to a Radio type Transmitting Alarm 180.

The alarm 180 can be used to broadcast an alert by mediums such as radio frequency, cellular type phone frequency, television signals, and the like, to remote locations, and the like. Additionally or alternatively, the invention can include an Alarm 190, such as a visible alarm(night light), an audible alarm such as but not limited to a bell, and the like, and combinations, thereof. Alarm 80 can also send alarm signals by other mediums such as but not limited to lasers, cables, wires, wireless mediums, and the like, and combinations thereof. When the Alarm visual and/or audible 190 and Radio type Transmitting Alarm 180 have alerted personnel and it is desired to either conserve the power of the DC Battery 200 or simply to silence the alarms, the Power Switch Manual Over-ride 100 is used. Both the Photo-Electric Cell Switch 160 and the Motion Sensor Switch 170 must be closed if current is to be supplied to the Anti-Carcinogenic™ Light Source 120. In the case of the Photo-Electric Cell Switch 160 such closing would occur only if no ambient, conventional light were detected. In the case of the Motion Sensor Switch 170 such closing would occur only if the presence of a human or a large animal were detected.

As indicated, a purpose of the Anti-Carcinogenic™ Night Light is to supply usable, non-carcinogenic™ light to humans or large animals moving in an otherwise darkened area, thereby to avoid a need for night lights emitting carcinogenic™ light.

The Anti-Carcinogenic™, CancerSafe™, or CancerGuard™ Light embodiments can be fabricated in a variety of sizes and configurations, such as but not limited to elliptical, oval, round, or square. The invention embodiments can be fabricated using a variety of light sources of different sizes and illuminating capacity. However, each of the novel light sources, such as but not limited to a bulb, tube, light-emitting diode, or L. E. D, or other light source unit would display the copyrighted legend, "Anti-Carcinogenic™ Night Light—Wavelengths 760 to 610 nm only—CancerSafe™, or CancerGuard™."

Two (2) switches can be aligned in series to activate the CancerSafe Night Light 120 shown in FIG. 1. The first switch 60 can be a photo-electric cell sensitive to ordinary ambient light, such as but not limited to daylight visible conditions, and the like, and/or when other visible light is already visible. This switch renders the night light inoperative by opening to interrupt the light's interior circuitry whenever ambient light is available. When ambient light is not available the interior circuit is closed by the photo-electric cell switch and the Anti-Carcinogenic™, CancerSafe™, or CancerGuard™ Night Light is thus ready to be activated by closure of the second switch. This switch, 130 can be a motion sensor switch, which also opens to interrupt the light's interior circuitry, only closing when a human or other large animal moves into its monitored field.

If designed as a night light to be plugged into common wall receptacles, the Anti-Carcinogenic™, CancerSafe™, or CancerGuard™ Night Light itself can provide one or more extra receptacle outlets 90, 95 so that other electrical or electronic appliances may conveniently be plugged into it and thereby connect to the same source of current. But if a current failure has occurred and the night light is operating on its back-up battery supply, no current would be supplied to these other appliances.

The Anti-Carcinogenic™, CancerSafe™, or CancerGuard™ Light has a manual over-ride switch 100 on its exterior so that it may be shut off altogether. This will save the back-up batteries if they are in use and it will silent the alarm and alarm transmitting mechanisms if they have been actuated.

The Anti-Carcinogenic™, CancerSafe™, or CancerGuard™ Night Light can be placed in, or adjacent to, areas customarily darkened either for sleeping or simply to save energy. In operation it will provide non-carcinogenic illumination whenever needed, without disrupting the secretions of the pineal glands of those exposed to it. It will extinguish itself when not needed, when ambient light is available and when the movement sensor indicates that there are no persons or large animals in the monitored area.

In the event of any of the dangerous circumstances that the Anti-Carcinogenic™ CancerSafe™, or CancerGuard™ Night is equipped to monitor, audible or visible alarms would be triggered and, if desired, also transmitted by means of radio energy, optical fiber, or laser beam to a centrally located emergency station. If normally supplied main line power is unavailable, the internal back-up battery or batteries would power these alarm signals. The monitored circumstances would include power failure, or the detection of dangerous pre-determined levels of smoke, heat, oxygen, carbon dioxide, carbon monoxide, radon, propane, radiological, bacteriological or other noxious, poisonous, or contagious substances. Its monitoring detectors and sensors could also include microphones to detect screams or cries for assistance, which might occur in muggings, medical emergencies, panics, school shootings, or other violent episodes.

The prevention of falls by the elderly has been designated a matter of Federal concern. In the absence of ambient light and the presence of persons or animals moving in the monitored area, the Anti-Carcinogenic™, CancerSafe™, or CancerGuard™ Night Light provides useful visual light to prevent accidents due to collisions with obstructions or falls on stairs. Falls are a major cause of elderly people precipitously declining in health and consequently becoming dependent on their families and public institutions.

In the event of a power failure, in addition to providing audible or visual alarm signals, and transmitting an alarm signal by laser, optical fiber, or radio energy, the Anti-Carcinogenic™, CancerSafe™, or CancerGuard™ Night Light would override both of its two main (2) switches, that is, the photo-electric cell switch and the motion sensor switch, and come on continuously, operating on battery power.

Figure 3:
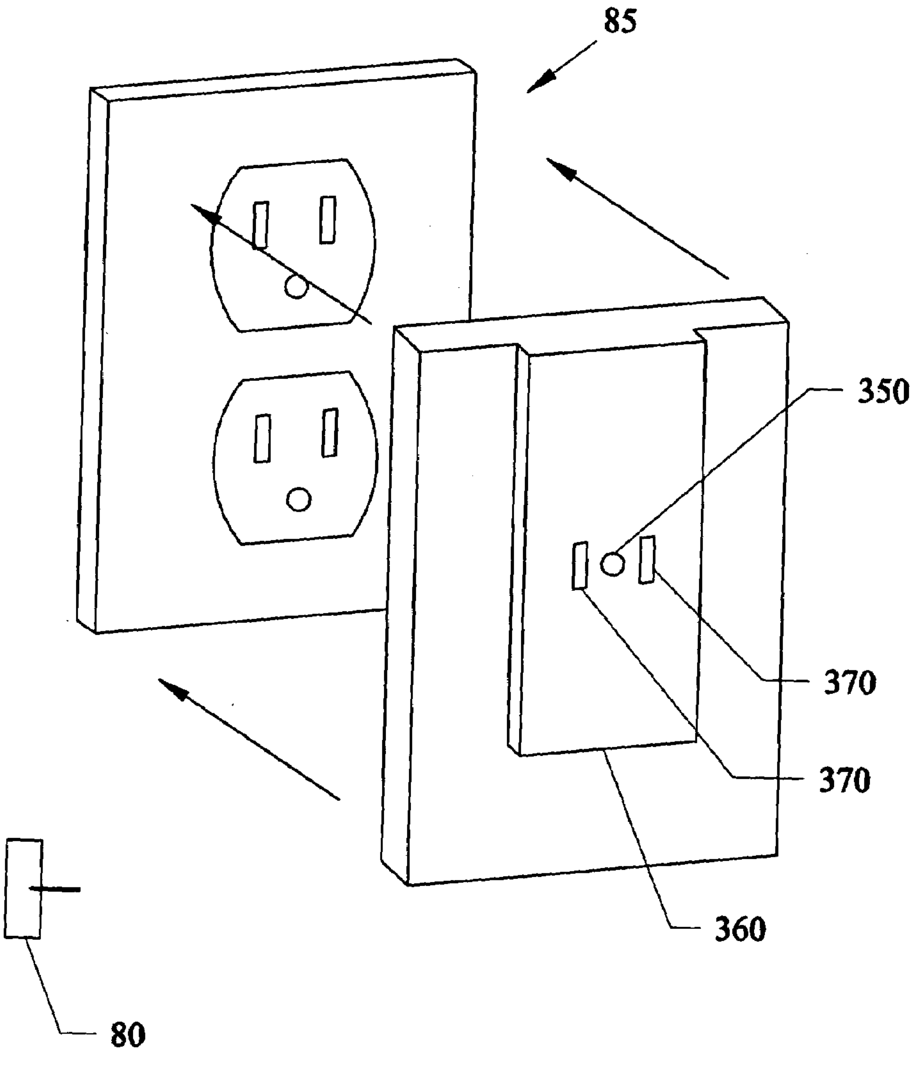
FIG. 3 shows a flexible filler plate for the Anti-Carcinogenic™ Night Light of FIG. 1.

FIG. 3 shows a flexible filler plate for the Anti-Carcinogenic™ Night Light of FIG. 1. The Flexible Filler Plate is designed to replace a standard Receptacle Box Cover Plate 85. The Flexible Filler Plate has a Raised Plane 360 congruent with and fitting into the Anti-Carcinogenic™ Night Light's Back Recess 110, shown in FIG. 1. By allowing the Anti-Carcinogenic™ Night Light to fit closer against the Receptacle Box into which it is plugged, the Flexible Filler Plate acts like a gasket.

In the event of a power overload or a short circuit, this relatively tight, gasket tight fit should prevent sparks from escaping from the inside of the Receptacle Box, thereby preventing an explosion in the presence of an explosive atmosphere. Note that the back of the Outer Case 10, shown in FIG. 1, is enclosed so sparks cannot escape from there.

Also note that the other openings in the Outer Case 10, the Atmosphere Sample Intake 50 and the Atmosphere Sample Exhaust 20, are protected by Flame Proof Screen(s) 140. The Flexible Filler Plate is held in place by the Child-Safe Screw 80 which passes through its Plate Securing Hole 350 and is screwed into the threaded hole in the center of the Receptacle Box. This threaded hole normally receives a screw holding the Protective Cover Plate 95 in place. The Flexible Filler Plate has a Raised Plane 360 congruent with the Anti-Carcinogenic™ Night Light's Back Recess 110, as shown in FIG. 1. The Receptacle Prongs 70 of the Anti-Carcinogenic™ Night Light pass through the Prong Access Port(s) 370.

Anti-Carcinogenic Refrigerator Light

Figure 4:
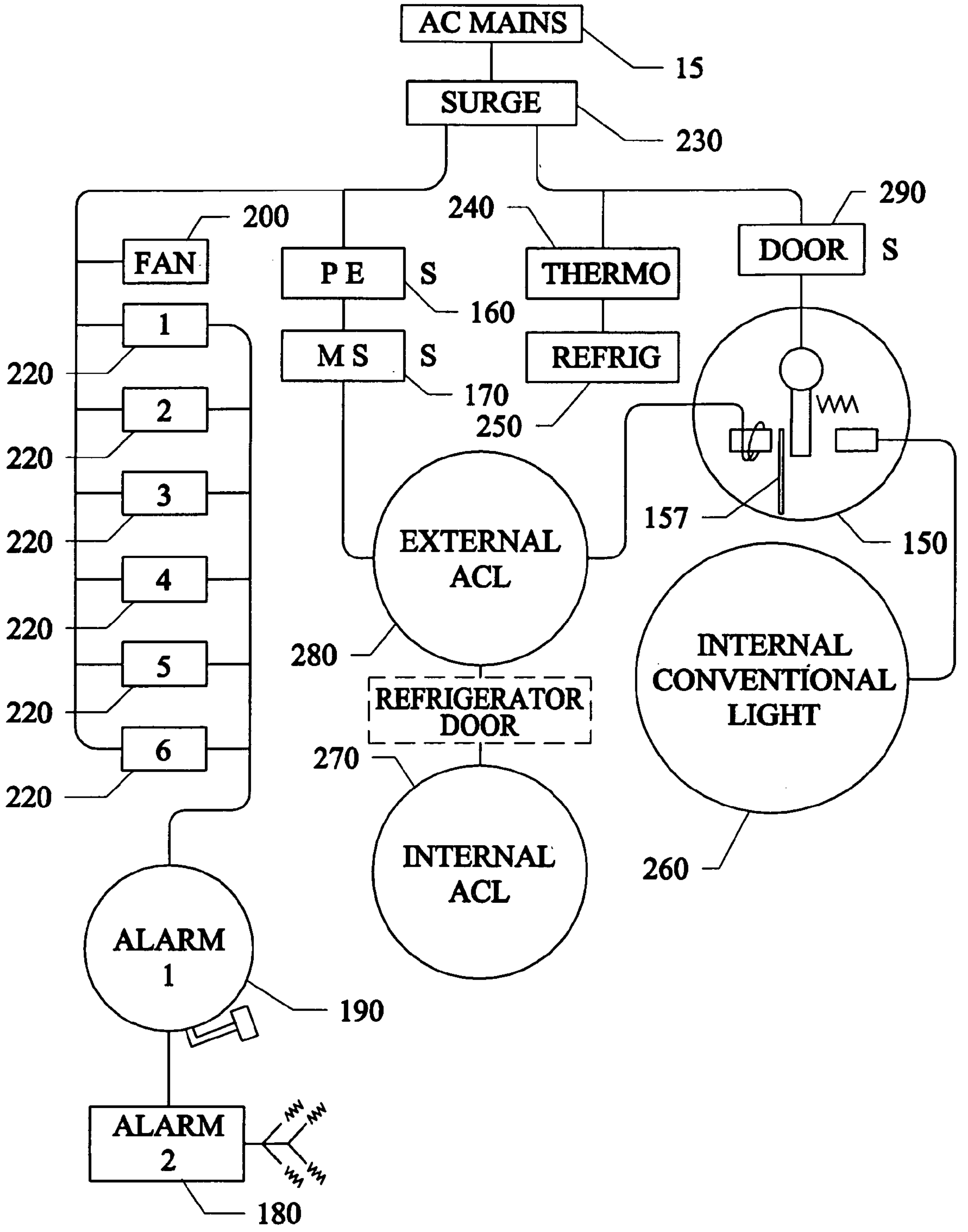
FIG. 4 is an electrical flow diagram for the Anti-Carcinogenic™ Refrigerator light.

FIG. 4 is an electrical flow diagram for an Anti-Carcinogenic™ Refrigerator light. The Anti-Carcinogenic™ light for a refrigerator, or other internally lighted cabinet or locker controlled by a door switch, requires an AC Power Supply 15. This is led directly to an AC(alternating current) Surge Protector 230 and thence to four (4) branch circuits. As seen in FIG. 4, the circuit furthest to the left leads to the Fan 200, then to six (6) Monitor Detectors 220(previously described) for use in detecting substances such as but not limited to dangerous gases, vapors, smoke, radiological, or biologically active substances, and the like, and then to the Bell Alarm 190 and the Radio Transmitting Alarm 180.

The circuit second from left leads to the Photo-Electric Cell Switch 160, the Motion Sensor Switch 170, the External Anti-Carcinogenic™ Light Source 280 and then to the Internal Anti-Carcinogenic™ Light Source 270 and an electromagnet within the Electro-Magnetic Switch 150. A Dielectric Short Circuit Barrier 157 prevents current from the External Anti-Carcinogenic™ Light Source 280 reaching across the Electro-Magnetic Switch 150 to the Refrigerator Door Switch 290 circuit. When energized, the Electro-Magnetic Switch 150 opens against a metallic spring in the switch, thereby preventing a conventional Refrigerator Door Switch 290 from energizing the refrigerator's conventional Internal Light 260.

The circuit third from left leads to the Refrigerator Thermostat 240 and to the Refrigeration Mechanism 250. Note that the External Anti-Carcinogenic™ Light Source 280 and the Internal Anti-Carcinogenic™ Light Source 270 are connected so both are illuminated at the same time.

The circuit fourth from the left, that is, on the right side of FIG. 4, supplies current to the Refrigerator Door Switch 290 and then to the aforementioned Electro-Magnetic Switch 150. As noted, during the day or whenever the room in which the refrigerator operates is conventionally illuminated, the Electro-Magnetic Switch 150 is kept closed by a metallic spring so that when the door of the refrigerator is opened, the conventional Internal Light 260 is illuminated to display its contents. Also during the day, the Photo-Electric Cell Switch 160 would be open to prevent current from reaching the Motion Sensor Switch 170 and the Anti-Carcinogenic™ Light Sources 280, 270. However, when the room is darkened, as detected by the Photo-Electric Cell Switch 160, and the movement of a human or large animal is detected by the Motion Sensor Switch 170, then current would be supplied to both Anti-Carcinogenic™ Light Sources 280, 270 and the electro-magnet in the Electro-Magnetic Switch 150.

Furthermore, the conventional Internal Light 260 of the refrigerator would not light up, even though the Door Switch 230 is closed by opening the refrigerator door, because the circuit from the AC Power Supply 15 is broken at the Photo-Electric Cell Switch 160.

A further refinement would connect the Refrigerator Internal Anti-Carcinogenic™ Light Source 270 to the Refrigerator Door Switch 290, or to a second Refrigerator Door Switch, so that the Internal Anti-Carcinogenic™ Light Source 270 would not be energized even though the External Anti-Carcinogenic™ Light Source 280 was energized. But this would not be necessary for refrigerators operating in ordinary installations.

The purpose of the Anti-Carcinogenic™ light for a refrigerator or other internally lighted cabinets or lockers, described in reference to FIG. 4, is to prevent a flood of carcinogenic™ light when a sleepy person moves into a darkened room and opens a refrigerator or other internally lighted cabinet.

This embodiment can include a conventional refrigerator fitted with the Anti-Carcinogenic™, CancerSafe™, or CancerGuard™ Night Light on its exterior. This Night Light would be wired into the refrigerator's internal light so that if the external Anti-Carcinogenic™ Night Light is on, when the refrigerator door is opened the interior illumination would also be by Anti-Carcinogenic™ Light. An external photo-electric cell switch would direct current to either the conventional interior white light or to an interior CancerSafe light when the refrigerator door is opened.

When there is conventional ambient light in the kitchen and the refrigerator door is opened, the photo-electric cell on the outside of the refrigerator causes the switch to which it is connected to supply electricity to the white interior light only. However, in the absence of such conventional ambient light in the kitchen, when the kitchen is substantially dark, and the refrigerator door is opened, then the photo-electric cell controlled switch on the outside of the refrigerator would direct current only to the Anti-carcinogenic™ Light. People arising from sleep at night frequently examine the contents of their refrigerators before returning to sleep. When they open the refrigerator door, however, they typically receive a blinding dose of white light from the bulb inside the refrigerator. In the context of a darkened area adjacent sleeping accommodations, this light disrupts the pineal gland's production of melatonin and is consequently carcinogenic. The bright white light will also thoroughly awakens nocturnal wanderers, uncomfortably blinding them and making it difficult for them to return to sleep.

Anti-Carcinogenic Clock/Watch Light

Figure 5:
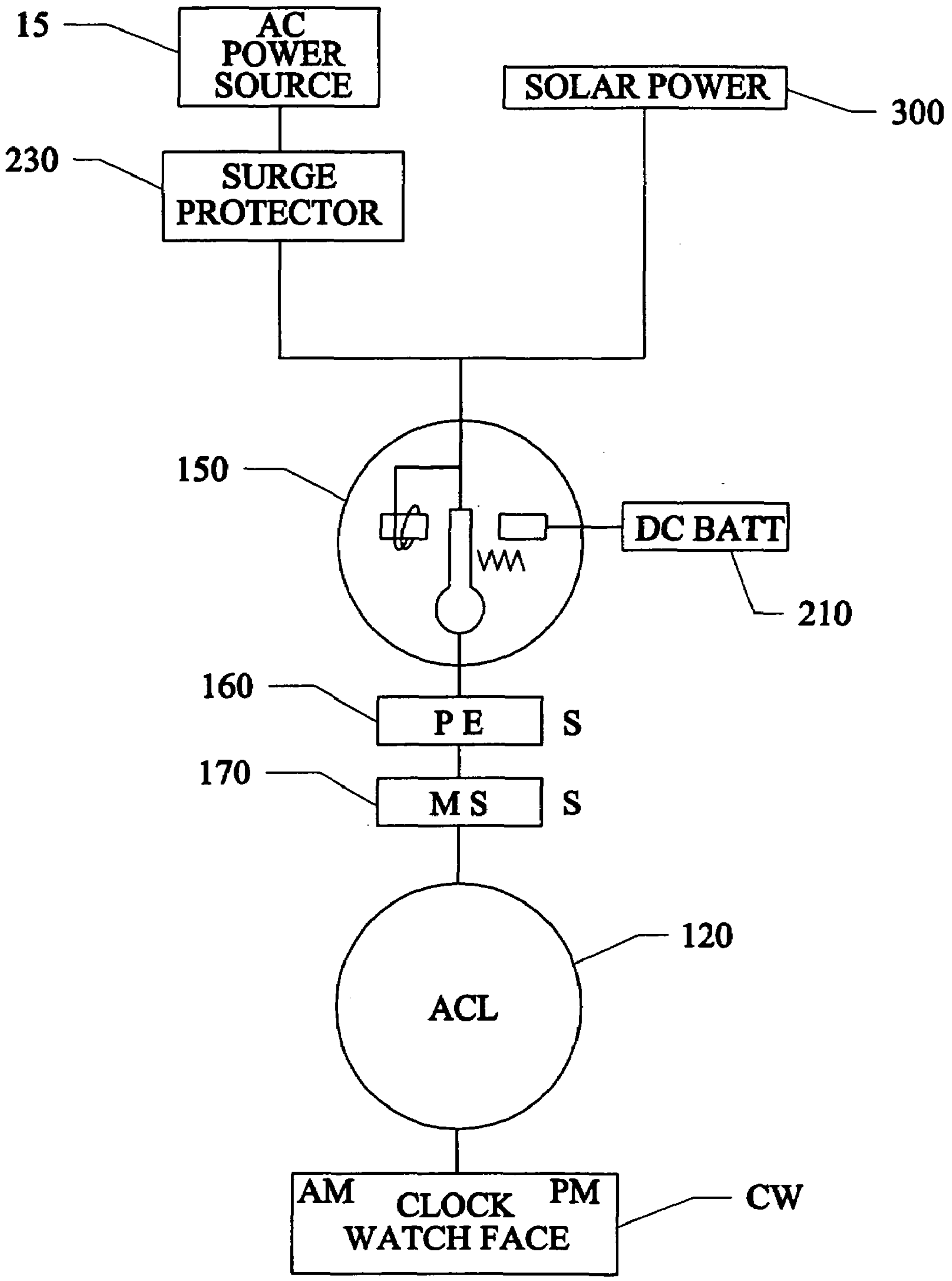
FIG. 5 is an electrical flow diagram for the Anti-Carcinogenic™ Clock/Watch light.

FIG. 5 is an electrical flow diagram for the Anti-Carcinogenic™ light for a Clock/Watch. The Anti-Carcinogenic™ Clock or Watch can be connected to an AC Power Supply 15 the current of which is kept constant by an AC(alternating current) Surge Protector 230. Alternatively, the novel clock-watch can be connected to a Solar Power Source 300. In either case current from these sources is led to an Electro-Magnetic Switch 150 (such as that previously described above) in such a manner that should these sources of power fail, a DC Battery 210 would supply current. This is contrived by converting a portion of the AC Power Supply 15 to Direct Current and using it to energize an electromagnet within the Electro-Magnetic Switch 150. Thus, in the event that both the AC Power Supply 15 and the Solar Power Source 300 are unavailable, D C Battery 210 current would be supplied.

The assured power supply can be led to a Photo-Electric Cell Switch 160 and then to a Motion Sensor Switch 170. If the location if which the Anti-Carcinogenic™ Clock or Watch is displayed is dark, then the Photo-Electric Cell Switch 160 will be closed to allow current to pass. If the Motion Sensor Switch 170 is similarly closed due to its sensing the movement of a human in its environs, then this switch, too, will allow current to pass, in which case the Anti-Carcinogenic™ Light Source 120 will illuminate the clock or watch face, CWF. Thus, in daylight or normal illumination the Anti-Carcinogenic™ Light Source 120 would not be lit, and even in the dark, if no motion by a human was detected, the Anti-Carcinogenic™ Light Source 120 would not be lit up.

A purpose of this embodiment is to assure that whenever the Anti-Carcinogenic™ Clock or Watch face CWF is displayed in an otherwise darkened space, and human movement is discerned within that space, then an Anti-Carcinogenic™ Light Source 120 would be available by which to read the timepiece. This invention would eliminate the need for a time conscious person to employ a separate Anti-Carcinogenic™ light source.

Electric or other light emitting wrist watches commonly display a night light to enable the dial to be read in the dark. These lights are invariably outside the range of wavelengths that describe Anti-Carcinogenic™ light and thus carcinogenic when used by sleepy people momentarily awakened from sleep. In this additional embodiment an Anti-Carcinogenic™ light is substituted to make the watch safe under these circumstances. Supplying an Anti-Carcinogenic™ light to illuminate the dial prevents the watch's dial light from disrupting the secretions of the pineal at night.

Anti-Carcinogenic Conversion Unit

Figure 6A:
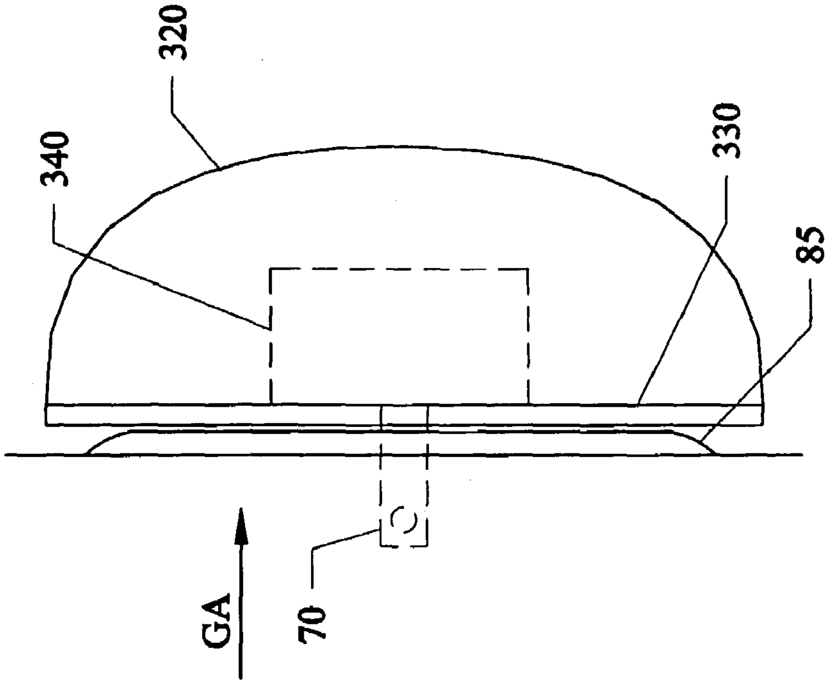
FIG. 6A is a side view of the conversion unit of FIG. 6 along arrow 6A.
Figure 6B:
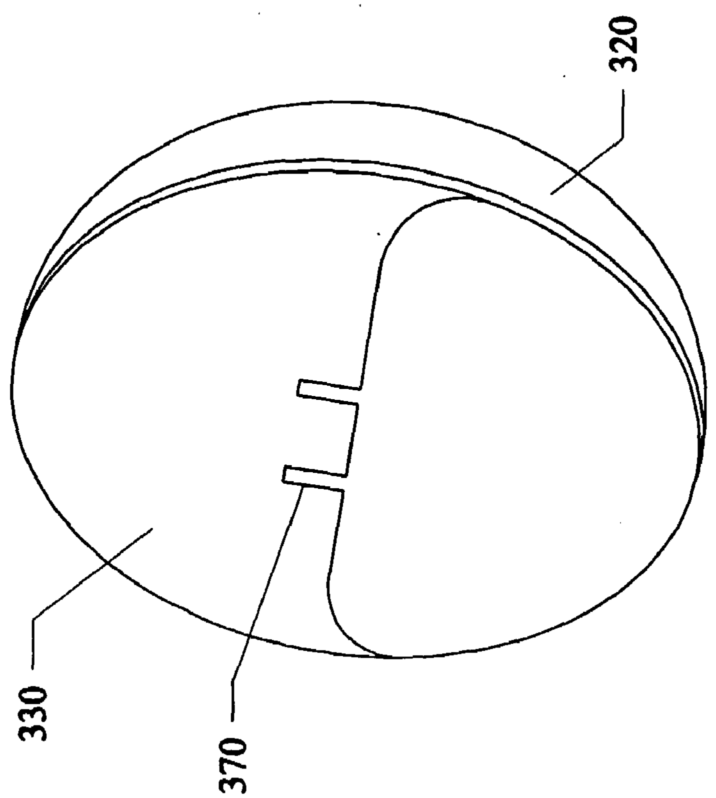
FIG. 6 is a perspective view of an Anti-Carcinogenic™ conversion unit.

FIG. 6 is a perspective view of an Anti-Carcinogenic™ conversion unit. FIG. 6A is a side view of the conversion unit of FIG. 6 along arrow 6A. The Conversion Unit is designed to fit over a conventional, Carcinogenic™ light emitting night light 340 and convert it into an Anti-Carcinogenic™ Light Source 120 by filtering out light of carcinogenic™ wavelengths. The novel device can consist of two (2) parts, a translucent Anti-Carcinogenic™ Filter Hood 320, and a Base Plate, 330. Two (2) Prong Access Ports 370 are situated in the middle of the Base Plate 330 and beneath them is an opening to allow the Base Plate 330 to be fitted over the convention night light. In use, the Conversion Unit can be positioned over the conventional night light 340 with the Base Plate 330 parallel to and above the Receptacle Box Cover 85. The Conversion Unit can then be slid down so that the bases of the Receptacle Prongs 70 fit into the two (2) Prong Access Slots) 370, thereby supporting it.

The conversion unit can be used to convert other types of light, such as lamps, and the like, having different sources, such as but not limited to fluorescent lights, LEDs(light emitting diodes), and the like.

OTHER EMBODIMENTS

A permanent system of CancerSafe™ or Anti-Carcinogenic™ Night Lights such as those described above can be installed as semi-permanent fixtures throughout areas adjacent to those customarily darkened for sleep. Such areas would include kitchens, hallways, stairways, cellars, and the passenger areas of conveyances on long trips, such as aircraft or ferries on long flights. In each covered area two (2) switches are aligned in series to activate the Anti-Carcinogenic™ or CancerSafe™ Night Lighting system. The first switch is a Photoelectric Cell Switch. It uses a photo-electric cell sensitive to ordinary visual light. This switch opens to deactivate portions of the system when ambient light of conventional wavelengths is available in monitored areas. When ambient light is not available, the interior circuit is closed and the light is ready to be activated by the second switch. The second switch, a motion sensor switch, closes to complete the circuit only when a human or animal of a predetermined size moves into the monitored field. Both switches must be closed to activate a portion of the system.

The above embodiments can be include Anti-Carcinogenic™ lighting fixtures that can be installed in discrete areas along baseboards, stairs, before doors, and at turns in the traffic pattern within a dwelling or vehicle. If an area covered and monitored by the Anti-Carcinogenic™ Night Lighting system is darkened, electrical power is automatically provided to the night lighting system. However, the system does not light to supply Anti-Carcinogenic™ light until motion sensors in each discrete covered or monitored area sense the presence of a person or an animal of predetermined size. Thus, as a person rises from sleep and moves from bedroom to bedroom, or to adjacent areas, these spaces are automatically illuminated with Anti-Carcinogenic™ light.

These additional applications of the invention have the further advantage of providing emergency lighting which would allow people to escape in the event of fire, smoke, or other hazardous change in the interior environment of the dwelling.

In the event of a power failure, the novel embodiments of the invention could override both of its two (2) switches and come on continuously, operating on battery power.

This novel invention can also provide an automatic burglar deterrent system. An intruder's entrance and movement through a structure would be seen from outside the house as the rooms light up and this light is seen through the windows. The intruder's progress could also be seen on closed circuit television, and be videotaped within the house.

An additional embodiment of the invention is the provision of ruby-colored or other red-colored plastic or glass doors or drapes of cover the windows of sleeping spaces and areas adjacent to them. Double doors arranged so that the external door, opening to the areas in carcinogenic light, would have to be closed before an internal door, opening to sleeping spaces and areas adjacent to them would have to be closed areas could be opened. The reason for this is that, in high latitude areas and at certain times of the year, residences and dormitories are completely bathed in light for most of the day and great portions of the night. This also occurs in urban areas at night where there is a great deal of light pollution. The result is that the bodies and eyes of the inhabitants of these areas are frequently exposed to the carcinogenic wavelengths of light during their customary hours of sleep when they are sleeping, sleepy, trying to sleep.

Translucent plastic or glass doors or drapes, ruby-colored or of some other shade of red to transmit only Anti-Carcinogenic™ light, can be deployed within the structures around all windows and doors. This will prevent stray rays of carcinogenic light from entering sleeping spaces and areas adjacent to them.

Limiting the wavelengths of visible light perceived by sleeping or sleepy people during customary sleeping hours to the range of approximately 760 to approximately 610 nanometers can and will reduce the incidence of cancer, which is a disaster for individuals and a huge burden for societies all over the world.

Light pollution of the sky, especially in urban areas, is increasingly seen to be harmful and not merely a disturbing problem. It has been the subject of major legislation in the State of New York, for example. Light pollution of the nighttime sky and of urban areas in general may well be a major cause of cancer. The present invention argues such a connection is possible, especially when persons who are sleeping, have been sleeping, or are about to fall asleep are exposed to carcinogenic light. In any event, light pollution within the home and dormitory is probably a greater problem than it is in the sky outside the home.

Certain areas of the United States have been specially associated with high rates of breast cancer, notably the San Francisco area of California. The areas cited are generally affluent where inhabitants can well afford the expense of night lights within the home. These are also areas that are more likely to invest in outside security lighting. Light from outside security lighting usually penetrates or floods into the home, with the consequences that are the concern of this invention.

The monitors in the above embodiments can be used to alert inhabitants in the event of terrorism attacks where substances such as noxious/poisonous materials are released by terrorism elements. The alarms can include notifying remote sites such as law enforcement, such as but not limited to fire, rescue, police, FBI(Federal Bureau of Investigation), Home Land Security, and the like.

The invention embodiments can also be used with computer type security systems in residences and commercial facilities. For example, the invention embodiments can be used with "Smart" type systems where the lights can be programmed for being switched on and off, and their activation times recorded and/or monitored for activating alarms, and the like.

While the above description contains many specificities, these should not be construed as limitations on the scope of the invention, but rather as exemplifications of an preferred embodiment thereof. Many other variations on the use of non-carcinogenic light are possible. For example, the instrument panels of vehicles, and such machinery as must be monitored in less than ordinary illumination, might make use of light limited to the above wavelengths.

Accordingly, the scope of the invention should be determined not by the embodiments provided, but by the appended claims and their legal equivalents.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. An anti-carcinogenic night light, comprising:

a light for emitting a visible light emission having a wavelength between approximately 610 and approximately 760 nanometers;

a power source for the light; and a light sensor connected between the light and the power source for switching off the light when ambient light is detected, and for switching on the light when ambient light is not detected, wherein the light is used as a night light emits a safe and non-carcinogenic visible light emission in a darkened or sem-darkened environment.

2. The night light of claim 1, wherein the power source includes:

a plastic case for housing the night light; and a plug extending from the case for connecting the night light to a wall outlet power source.

3. The night light of claim 1, wherein the power source includes:

a plastic case for housing the night light; and a battery power supply for supplying power to the night light.

4. The night light of claim 1, further comprising:

a motion sensor connected to the light sensor which activates the light when motion and lack of ambient light is detected.

5. An anti-carcinogenic night light, comprising:

a light for emitting a visible light emission having a wavelength between approximately 610 and approximately 760 nanometers;

a power source for the light;

a monitor sensor selected from at least one of a group consisting of:

an electric power failure sensor, a smoke detector, a heat detector, an oxygen detector, a carbon dioxide detector, a carbon monoxide detector, a radon detector, a propane detector, a radiological substance detector, a bacteriological substance detector, a noxious fume detector, a poisonous gas detector, and a sound detector; and an alarm for being triggered when a pre-selected threshold level is detected by the monitor sensor, the alarm being selected from at least one of a group consisting of: a visible alarm, an audible alarm, and a remotely transmitted alarm, wherein the light is used as a night light emits a safe and non-carcinogenic visible light emission in a darkened or sem-darkened environment.

6. An anti-carcinogenic night light, comprising:

a light for emitting a visible light emission having a wavelength between approximately 610 and approximately 760 nanometers;

a power source for the light; and a refrigerator door for mounting the light inside of the refrigerator door, so that the light activates when the refrigerator door is opened, wherein the light is used as a night light emits a safe and non-carcinogenic visible light emission in a darkened or sem-darkened environment.

7. An anti-carcinogenic night light, comprising:

a light for emitting a visible light emission having a wavelength between approximately 610 and approximately 760 nanometers;

a power source for the light; and a refrigerator door for mounting the light outside and exterior to the refrigerator door, so that the light emits outside and exterior to the refrigerator door, wherein the light is used as a night light emits a safe and non-carcinogenic visible light emission in a darkened or sem-darkened environment.

8. An anti-carcinogenic night light, comprising:

a light for emitting a visible light emission having a wavelength between approximately 610 and approximately 760 nanometers;

a power source for the light; and a clock face over the emission from the light, for supplying visible light to the clock face, wherein the light is used as a night light emits a safe and non-carcinogenic visible light emission in a darkened or sem-darkened environment.

9. An anti-carcinogenic night light, comprising:

a light for emitting a visible light emission having a wavelength between approximately 610 and approximately 760 nanometers;

a power source for the light; and a wrist watch face over the emission from the light, for supplying visible light to the wrist watch face, wherein the light is used as a night light emits a safe and non-carcinogenic visible light emission in a darkened or sem-darkened environment.

10. An anti-carcinogenic night light, comprising:

a light for emitting a visible light emission having a wavelength between approximately 610 and approximately 760 nanometers;

a power source for the light; and an adapter for attaching the anti-carcinogenic light to an existing night light, and for converting the existing night light to emit visible light solely between the wavelength of approximately 610 to approximately 760 nanometers, wherein the light is used as a night light emits a safe and non-carcinogenic visible light emission in a darkened or sem-darkened environment.

11. A method for emitting anti-carcinogenic light emission from a night light, comprising the steps of:

supplying power to a light source;

emitting a visible light between the wavelength of approximately 610 to approximately 760 nanometers from the light source, in a darkened or sem-darkened environment, as a night light; and preventing disruptions of secretions of pineal glands of sleeping, sleepy or dozing humans and animals that are located in the darkened or sem-darkened environments where the night light is located.

12. The method of claim 11, further comprising the step of:

plugging the night light into an existing wall outlet for the step of supplying power to the light source.

13. The method of claim 11, further comprising the step of:

supplying power to the night light from a battery power source.

14. The method of claim 11, further comprising the step of:

detecting ambient surrounding light to switch off the night light; and switching on the night light when no ambient surround light is detected.

15. The method of claim 11, further comprising the step of:

sensing motion of a moving object selected from at least one of: a human and a animal, so that the night light is switched on when both motion is sensed and no surrounding ambient light is detected.

16. The method of claim 11, further comprising the step of:

monitoring a condition selected from at least one of a group consisting of:

an electric power failure sensor, a smoke detector, a heat detector, an oxygen detector, a carbon dioxide detector, a carbon monoxide detector, a radon detector, a propane detector, a radiological substance detector, a bacteriological substance detector, a noxious fume detector, a poisonous gas detector, and a sound detector; and triggering an alarm when at least one of the monitored conditions is detected, the alarm being selected from at least one of a group consisting of: a visible alarm, an audible alarm, and a remotely transmitted alarm.

17. The method of claim 11, further comprising the step of:

attaching the night light inside of a refrigerator door; and activating the night light when the refrigerator door is opened.

18. The method of claim 11, further comprising the step of:

attaching the night light outside and external to a refrigerator door; and activating the night light during the darkened or sem-darkened environment.

19. The method of claim 11, further comprising the step of:

attaching the light source to an existing night light; and converting the existing night light to emit within the wavelength of between approximately 610 to approximately 760 nanometers with the night light.

* * * * *